United States Patent
Morris-Watson et al.

(10) Patent No.: US 9,192,688 B2
(45) Date of Patent: Nov. 24, 2015

(54) INACTIVATION OF PATHOGENS

(76) Inventors: Michael Edward Morris-Watson, Suffolk (GB); Duncan James Foster, Suffolk (GB)

( * ) Notice: Subject to any disclaimer, the term of this patent is extended or adjusted under 35 U.S.C. 154(b) by 506 days.

(21) Appl. No.: 13/496,029

(22) PCT Filed: Sep. 13, 2010

(86) PCT No.: PCT/GB2010/051523
§ 371 (c)(1),
(2), (4) Date: Jun. 4, 2012

(87) PCT Pub. No.: WO2011/030162
PCT Pub. Date: Mar. 17, 2011

(65) Prior Publication Data
US 2012/0228412 A1    Sep. 13, 2012

(30) Foreign Application Priority Data
Sep. 14, 2009    (GB) .................................. 0916016.9

(51) Int. Cl.
| A61L 9/00 | (2006.01) |
| F26B 5/04 | (2006.01) |
| F26B 21/06 | (2006.01) |
| A61L 2/20 | (2006.01) |
| A61L 11/00 | (2006.01) |

(52) U.S. Cl.
CPC *A61L 2/208* (2013.01); *A61L 11/00* (2013.01)

(58) Field of Classification Search
CPC .......... A01N 1/00; A01N 1/0215; A61L 2/00; A61L 2/208; B05D 1/02

USPC ...................... 34/403, 437; 422/1, 28, 32–33; 435/267; 261/287, 293, 443; 623/920
See application file for complete search history.

(56) References Cited

U.S. PATENT DOCUMENTS

| 3,612,411 A | 10/1971 | Oetjen | |
| 5,213,774 A * | 5/1993 | Noetzel | 422/292 |
| 5,286,448 A | 2/1994 | Childers | |
| 5,445,792 A | 8/1995 | Rickloff | |

FOREIGN PATENT DOCUMENTS

| WO | 93/25329 | 12/1993 | |
| WO | 97/27882 | 8/1997 | |
| WO | WO 97/27882 * | 8/1997 | ................ A61L 2/20 |

OTHER PUBLICATIONS

International Search Report for corresponding patent application PCT/GB2010/051523 dated Nov. 12, 2010.

* cited by examiner

*Primary Examiner* — Monzer R Chorbaji
(74) *Attorney, Agent, or Firm* — Brinks Gilson & Lione; G. Peter Nichols

(57) ABSTRACT

A method of treating organic material including the steps of comminuting the material to achieve an average particle size of less than about 10 mm; drying the material to achieve a moisture content of less than about 40% (w/w); exposing the dried comminuted material to reduced pressure and contacting said dried comminuted material with gaseous hydrogen peroxide at reduced pressure.

9 Claims, 3 Drawing Sheets

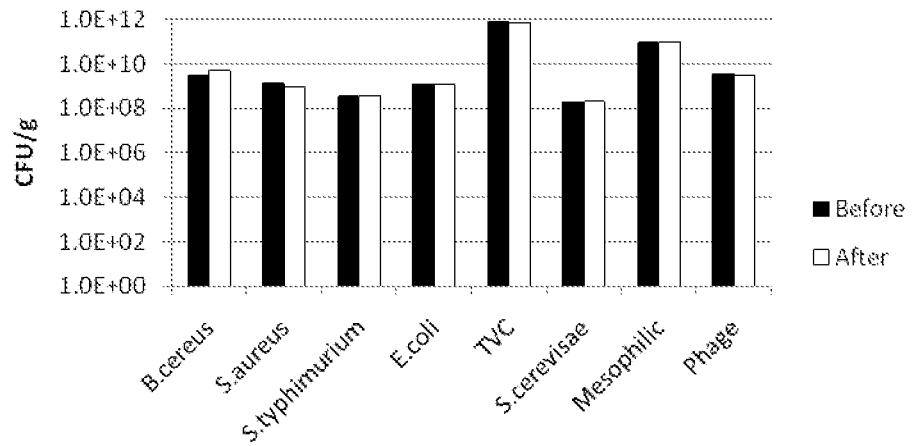
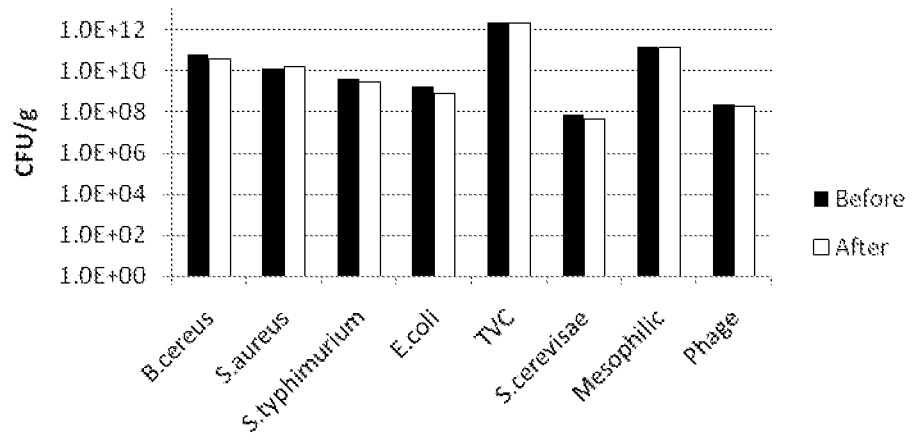

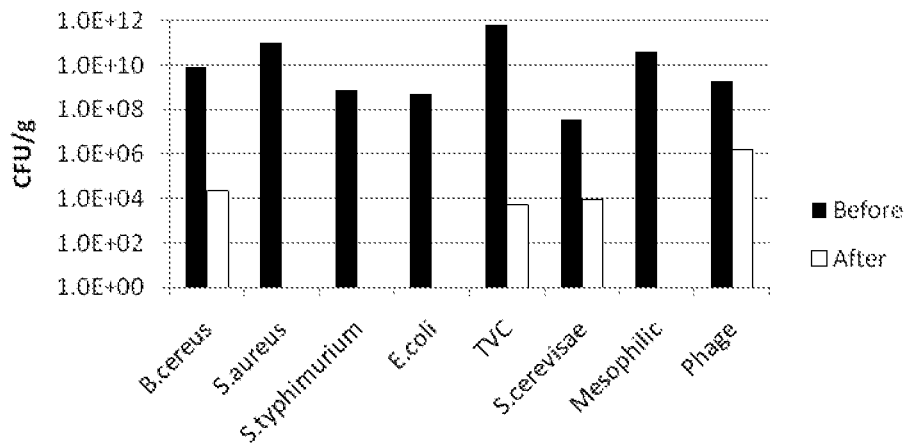
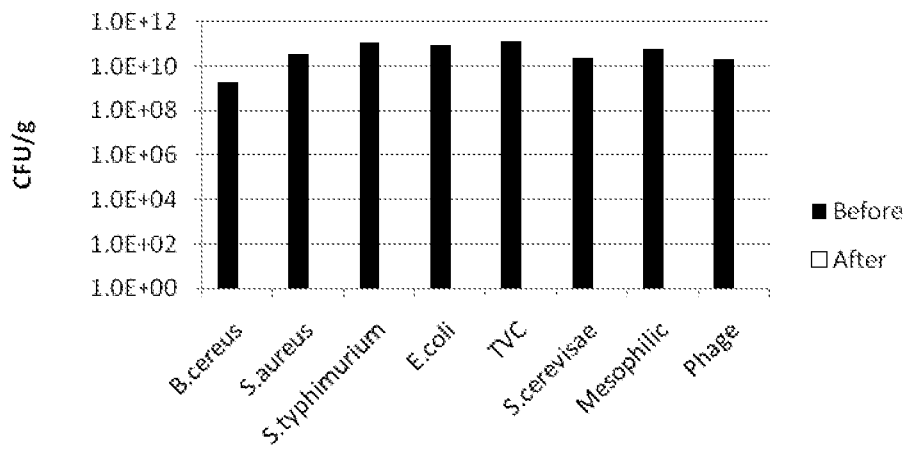

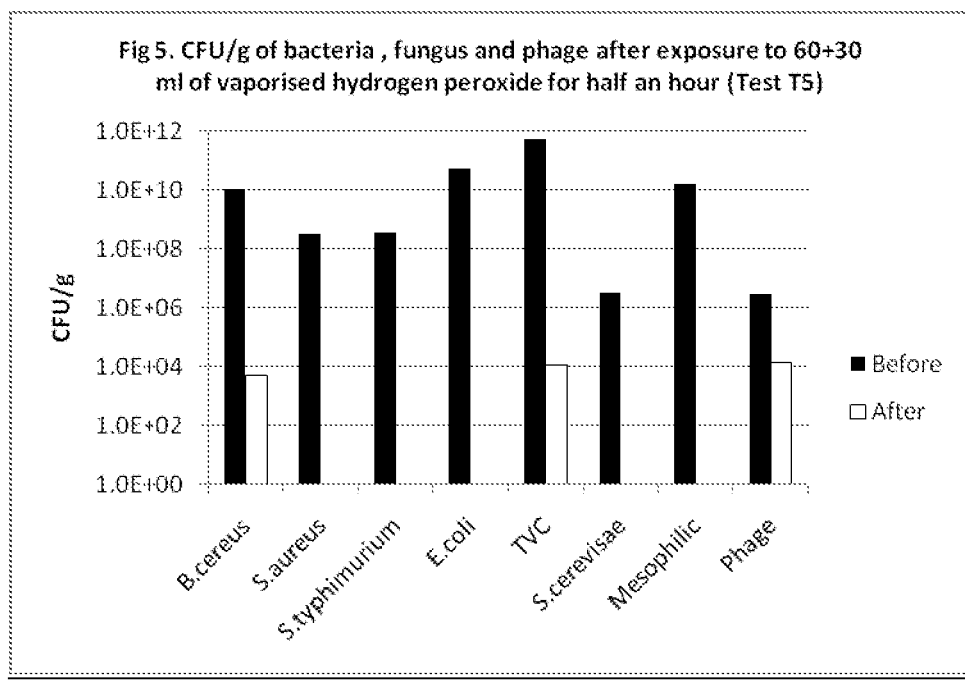

INACTIVATION OF PATHOGENS

This application is a national phase of International Application No. PCT/GB2010/051523 filed Sep. 13, 2010 and published in the English language.

FIELD OF THE INVENTION

The invention relates to improved methods for treating wet organic matter, or inorganic matter that has been biologically contaminated. In particular, it relates to methods for preparing and treating such material, such as human and animal remains and clinical waste, for disposal by burial, or to allow the sanitised inorganic matter to be sorted and recycled.

BACKGROUND AND PRIOR ART KNOWN TO THE APPLICANT

At present, cremation is the main process for the disposal of large animal carcasses and is often used for the disposal of bodies of dead humans. The process uses large quantities of fossil fuels and results in the discharge of large volumes of carbon dioxide to the atmosphere. This clearly has negative environmental consequences in relation to atmospheric $CO_2$. The other common method of disposal of such organic material is burial, and in the context of disposal of animal waste, often mass burial. This process has, however, possible negative consequences for soil contamination, and damage to watercourses, especially from mass animal burial sites.

Despite the high energy demand of the cremation process, burning of such animal remains has the advantage of killing any pathogens within the bodies, so preventing microbial contamination of the ground in which the ashes may be deposited. Such pathogens occur naturally in the digestive tract of animals, but particular pathogens may also be present in the material such as those that led to the death of the animal or person concerned. For example, if a person dies from septicaemia, their blood will contain high titres of human pathogens. Similarly, if a farm animal dies from a disease such as Foot and Mouth Disease or Bovine Spongiform Encephalopathy (BSE) the carcass would be potentially contaminated respectively with the virus or prion responsible for these diseases.

There are a number of different sources of such potentially contaminated organic material for which this process of inactivation of pathogens has application: disposal of human remains; disposal of fallen stock such as cattle and sheep; processing of abattoir waste; processing of food waste from production, wholesale and retail sources; disposal of waste from ships and boats; and the disposal of clinical waste from e.g. hospitals.

Alternative processes have been proposed, such as that described in international patent application WO 0140727 in which liquid nitrogen is used to freeze a body prior to mechanical disintegration, and subsequent drying. However, it is well known that liquid nitrogen freezing can actually act to preserve bacteria and other organisms.

An improved process is also described in the applicant's own earlier international patent application WO2008/129322. Whilst this process is effective, its action is most successful against Gram negative bacteria. If it is desired to treat material having a high load of Gram positive bacteria, yeasts, virus and prions, then further improvements are desirable.

It is an object of the invention, therefore, to provide alternative methods for disposal of animal and human bodies using lower energy input, and which result in a microbiologically acceptable material, at least reducing and preferably eliminating virus and prion material.

SUMMARY OF THE INVENTION

Accordingly, the invention provides a method of treating organic material including the steps of: comminuting said material, if required, to achieve an average particle size of less than about 10 mm; drying said material, if required, to achieve a moisture content of less than about 40% (w/w); exposing said dried comminuted material to reduced pressure; contacting said dried comminuted material with gaseous hydrogen peroxide at reduced pressure. The comminution stage may be required is the starting organic matter is larger than about 10 mm. Comminution may be carried out by chopping or cutting. A particularly preferred method, however, is to fracture or mill the organic material when it is in a frozen state, e.g. having been frozen with liquid nitrogen. The drying stage is required if the starting material has a moisture content of more than about 40% (w/w).

Preferably, said organic material is reduced to a particle size of less than about 5 mm. The inventors have found that such size reduction allows the gaseous hydrogen peroxide to penetrate further into the organic material, thereby rendering the process faster and more effective.

In any aspect of the invention, it is preferred that said organic material is dried to a moisture content of less than about 20% (w/w). The extra reduction in moisture content is beneficial to penetration of the hydrogen peroxide, and also reduces subsequent transport costs.

Also in any aspect of the invention, it is preferred that said drying is achieved by freeze drying. Freeze drying maintains an open pore structure in the organic material, thereby allowing the gaseous hydrogen peroxide to penetrate into the organic material.

Also in any aspect of the invention, it is preferred that said reduced pressure is below 10 kPa. Reducing the pressure to below about 10% of atmospheric pressure improves the penetration of the gaseous hydrogen peroxide into the organic matter. More preferably, the pressure is reduced to below 1 kPa. Most preferably, however, said reduced pressure constitutes a partial vacuum, i.e. effectively as close to a true vacuum as may be practically achieved on a commercial scale. A typical figure would be approximately 0.1 kPa.

Also in any aspect of the invention, it is preferred that said dried comminuted material is contacted with gaseous hydrogen peroxide at a level of at least 7.5 g $H_2O_2$ per kg of dried material. More preferably, said dried comminuted material is contacted with gaseous hydrogen peroxide at a level of at least 10 g $H_2O_2$ per kg of dried material.

Also in any aspect of the invention, it is preferred that said dried comminuted material is contacted with gaseous hydrogen peroxide at a rate of at least 0.1 g $H_2O_2$ per kg of dried material per second. The inventors have found that such rapid exposure to the gaseous hydrogen peroxide increases its effectiveness. More preferably, said dried comminuted material is contacted with gaseous hydrogen peroxide at a rate of at least 0.5 g $H_2O_2$ per kg of dried material per second.

Included within the scope of the invention is a method of treating organic material substantially as described herein, with reference to and/or as illustrated by any appropriate combination of the accompanying drawings.

BRIEF DESCRIPTION OF THE DRAWINGS

FIGS. 1 to 5 illustrate, graphically the reduction in viable count of a number of test organism before (solid bars) and after (open bars) various treatments described herein.

DESCRIPTION OF PREFERRED EMBODIMENTS

Experimental tests have been carried out to determine the effectiveness of the process in inactivating a range of organisms including bacteria, fungi, viruses and prions. Four bacteria were used in the trials: *Bacillus cereus, Staphylococcus aureus, Salmonella typhimurium* and *Escherichia coli*. *B. cereus* and *S. aureus* were chosen as examples of sporogenic and non-sporogenic Gram positive organisms respectively, each of which are linked to human disease. *S. typhimurium* and *E. coli* were chosen as examples of Gram negative organisms, each of which again are linked to human disease. The yeast *Saccharomyces cerevisiae* was chosen as an example of a eukaryotic micro-organism. To study the effect of the process on viruses, a bacteriophage hosted in *E. coli* strain G204 was employed.

In each of five trials (T1-T5), a sample of pork meat, used as a model of organic material, was comminuted to give an average particle size of about 5 mm and this was dried in a freeze dryer to below 20% (w/w) and then adjusted to give a moisture content of about 20% (w/w). 5 kg of this comminuted dried meat was inoculated with a cocktail of the organisms above, and mixed to achieve homogeneity.

The inoculated material was loaded into a freeze dryer, having a chamber volume of approximately 50 liters, to enable the pressure to be reduced to approximately 0.01 kPa (0.1 mBar).

In the first four trials (T1-T4), hydrogen peroxide was vaporised from a given volume of stock solution of 30% (v/v) $H_2O_2$ by use of a hydrogen peroxide vaporiser (Clarus L, available from Bioquell UK Limited, United Kingdom) and introduced to the freeze dryer chamber at a rate of about 30 ml of stock solution every 3-4 minutes.

For the fifth trial (T5), 30 ml of stock solution was vaporised into a holding vessel, and then this vaporised $H_2O_2$ was introduced rapidly into the chamber over a period of about 5 seconds. Then, a further 60 ml of stock solution was vaporised into the chamber, at a rate of about 30 ml of stock solution every 3-4 minutes.

The table below shows the details of each trial.

| Trial | Mass Meat (kg) | $H_2O_{2(aq)}$ (ml)[1] | $H_2O_{2(g)}$ (g)[2] | $H_2O_2$ (g/kg meat) | $H_2O_2$ Addition Rate (g/kg/s)[3] |
|---|---|---|---|---|---|
| T1 | 5 | 30 | 13.14 | 2.6 | 0.01 |
| T2 | 5 | 60 | 13.14 | 2.6 | 0.01 |
| T3 | 5 | 90 | 39.42 | 7.9 | 0.01 |
| T4 | 5 | 160 | 70.08 | 14.0 | 0.01 |
| T5 | 5 | 30 | 13.14 | 2.6 | 0.5 |
|   |   | 60 | 13.14 | 2.6 | 0.01 |

Notes:
[1] Volume of aqueous 30% (v/v) $H_2O_2$
[2] Mass of hydrogen peroxide (calculated from a density of 1.46 g/ml)
[3] Approximate mass of hydrogen peroxide added per kg of meat per second The gaseous hydrogen peroxide was left in contact with the organic material for 30 minutes. Four samples were taken from the organic material to determine the effect on the organisms by use of relevant selective media. Nutrient agar was used for determination of total viable count (at 37° C.) and total mesophilic count (at 30° C.). Malt extract agar (MEA) at 22° C. was used to detect fungal growth. Xylose lysine deoxycholate (XLD) agar was used to detect *Salmonella*, violet red bile for *E. coli*, *B. cereus* selective agar and Vogal-Johnson agars were used to selectively enumerate *B. cereus* and *S. aureus* respectively.

Results from the tests are shown in FIGS. 1 to 5. FIGS. 1 and 2 show that the test conditions T1 and T2 had little or no effect on any of the test organisms. FIG. 3 shows that the test conditions of T3 had a significant effect on the organisms with elimination of *S. aureus, S. typhimurium, E. coli* and generally mesophilic organisms. Other organisms experienced between a 3 and 6 logarithmic reduction in their numbers. FIG. 4 shows that the use of higher levels of gaseous hydrogen peroxide in trial conditions T4 led to a complete elimination of all test organisms.

In a particularly surprising result, FIG. 5 shows (by comparison to FIG. 3) that by increasing the rate at which the gaseous hydrogen peroxide is contacted with the organic material, the inactivation can be enhanced. The data show a particularly striking effect on the inactivation of *S. cerevisiae*.

In a further test, the treatment protocol of T5 was carried out to determine its effect on prion protein. In the test, 5 g of meat have a moisture content of 20% was contaminated with 100 ug of model prion protein (Abcam, UK) and mixed for 3 hours with a vortex mixer. Half of the contaminated sample was reserved as a positive control, and the other half was placed in a 50 ml beaker and subjected to the protocol of T5 (rapid exposure to 30 ml hydrogen peroxide vapour, followed by gradual exposure to 60 ml hydrogen peroxide vapour) within a freeze-drying chamber.

Following the treatment, the prion content of the sample and the control was determined by treating with first and second antibodies (Abcam, UK) before Western Blotting. The results indicate that prions are significantly destroyed by the treatment.

The invention claimed is:

1. A method of treating potentially contaminated waste material selected from disposal of human remains, disposal of fallen stock, processing of abattoir waste, processing of food waste from production, wholesale and retail sources, disposal of waste from ships and boats or disposal of clinical waste, including the steps of:
   comminuting said material, if required, to achieve an average particle size of less than about 10 mm;
   freeze drying said comminuted material, if required, to achieve a moisture content of less than about 40% (w/w);
   exposing said dried comminuted material to reduced pressure;
   contacting said dried comminuted material with gaseous hydrogen peroxide at reduced pressure.

2. A method according to claim 1 wherein said material is reduced to a particle size of less than about 5 mm.

3. A method according to claim 1 wherein said material is dried to a moisture content of less than about 20% (w/w).

4. A method according to claim 1 wherein said reduced pressure is below 10 kPa.

5. A method according to claim 4 wherein said reduced pressure constitutes a partial vacuum.

6. A method according to claim 1 wherein said dried comminuted material is contacted with gaseous hydrogen peroxide at a level of at least 7.5 g $H_2O_2$ per kg of dried material.

7. A method according to claim 6 said dried comminuted material is contacted with gaseous hydrogen peroxide at a level of at least 10 g $H_2O_2$ per kg of dried material.

8. A method according to claim 1 wherein said dried comminuted material is contacted with gaseous hydrogen peroxide at a rate of at least 0.1 g $H_2O_2$ per kg of dried material per second.

9. A method according to claim 8 wherein said dried comminuted material is contacted with gaseous hydrogen peroxide at a rate of at least 0.5 g $H_2O_2$ per kg of dried material per second.

\* \* \* \* \*